United States Patent [19]

Waits

[11] Patent Number: 5,178,631
[45] Date of Patent: Jan. 12, 1993

[54] BI-LEAFLET HEART VALVE PROSTHESIS WITH SHARED PIVOT RECESS

[75] Inventor: Charles T. Waits, Pflugerville, Tex.

[73] Assignee: Carbomedics, Inc., Austin, Tex.

[21] Appl. No.: 776,990

[22] Filed: Oct. 16, 1991

[51] Int. Cl.⁵ ............................................. A61F 2/24
[52] U.S. Cl. ................................ 623/2; 137/512.1; 137/527
[58] Field of Search ................. 623/2; 137/512.1, 527

[56] References Cited

U.S. PATENT DOCUMENTS

| | | | |
|---|---|---|---|
| 4,308,624 | 1/1982 | Klawitter | 623/2 |
| 4,328,592 | 5/1982 | Klawitter | 623/2 |
| 4,892,540 | 1/1990 | Vallana | 623/2 |

*Primary Examiner*—Ronald Frinks
*Attorney, Agent, or Firm*—John R. Merkling

[57] ABSTRACT

A bi-leaflet heart valve having pivot ears comprising frusto-conical segments, located substantially at a diametral edge of leaflet occluders of the valve. Pivots on adjacent edges of both occluders share a common recess in an annular body of the valve.

10 Claims, 2 Drawing Sheets

BI-LEAFLET HEART VALVE PROSTHESIS WITH SHARED PIVOT RECESS

BACKGROUND OF MY INVENTION

My present invention pertains to heart valve prostheses and in particular, to bi-leaflet mechanical heart valve prostheses using pivotable occluders.

DESCRIPTION OF RELATED ART

Various types of heart valve prostheses have been proposed, and many give generally satisfactory operation. One popular design for a heart valve prosthesis includes an annular valve body in which a pair of opposed leaflet occluders are pivotally mounted. The occluders are movable between a closed, mated position, blocking blood flow in an upstream direction and minimizing regurgitation, and an open position, allowing blood flow in a downstream direction.

Because hemodynamic energy alone moves the occluders of the heart valve between its open and closed positions, it is generally desireable to reduce dynamic friction losses which would needlessly burden the cardiac system. Static frictional forces are not significant in a well-designed heart valve if there are no surfaces normal to the leaflet's initial opening movement. A complete reversal of the flow direction initiates movement of the occluder away from the surfaces that constrain it from rotation. A certain amount of play in the pivot mechanism is necessary to assure that relatively small and fragile ends of the pivots do not bear the high loads the valve is exposed to when it is fully closed.

Over the countless number of operations of a heart valve, pivot ears and recesses are subjected to wear. For the reasons set forth in the U.S. Pat. No. 4,689,046, to Bokros, also assigned to the Assignee of my Application, spherical pivots and recesses are susceptible to significant amounts of "play" in directions lying in the plane of the leaflet and extending generally perpendicular to the diametrical edge thereof. It has been observed that relatively small amounts of wear adjacent the tip of the spherical pivot or the corresponding center portion of the recess results in a significant amount of lateral play, even for relatively minute amounts of increased "end play", that is, in directions generally parallel to the diametrical leaflet edge and extending along the hinge points of a leaflet. As a result of this laterial play, the motion and the sequence, especially the synchronous cooperation of the leaflets, become less well defined. As a result, performance of the leaflet may become erratic, as is evidenced, for example, by an asynchronous closure of the valve. While prior art heart valves have generally proven to be very reliable, and to have a projected life expectancy exceeding that of the patient, it is desirable to achieve increased margins of safety by providing a prosthesis which substantially exceeds reliability and performance requirements.

Several other improvements to heart valve prostheses are also desired. For example, it is desirable to impart a more rapid closing time to the leaflet occluders so as to reduce regurgitation. However, such quickening of the closing time should not be accompanied by an increase in noise during operation of the prosthesis, for example, as the leaflet occluders seat against the valve body to block regurgitation. Also, any rebounding of the leaflets should be controlled so as to prevent unnecessary wear, and to converse hemodynamic energy. Any decrease in valve closing time, therefore, should not contribute to rebounding of the leaflets.

In the past, leaflet occluders have occasionally been slightly undersized so as to allow a purging blood flow around them, even when the leaflets are closed. Such flows wash over edge surfaces of the leaflets and the valve body to prevent clotting that might occur at those locations. The hemodynamic energy of a patient, however, should be conserved. Accordingly, the amount of undersizing of the leaflet occluders must be accurately controlled. Such sizing, of course, depends upon the manufacturing tolerances which can be obtained for the selected geometry of the valve body as well as of the leaflet occluders. Since manufacturing costs are directly related to manufacturing tolerances, alternative arrangements for providing a purging flow around the leaflet occluders, particularly at their hinged connections to the valve body, in a manner which conserves hemodynamic energy, are still being sought.

The leaflet occluders of a heart valve respond to applied hemodynamic forces. In particular, forward and reverse blood flow exerts torsional forces on the occluders. These torsional forces act to open or close the occluders depending on the direction of flow. The magnitude of the torsional force is proportional not only to the magnitude of the flow of the blood, but also to the lever arm presented by the leaflet occluder. The size of a heart valve is, of course, selected to most nearly correspond to the physiology of a particular patient, nevertheless, the placement of pivots on the occluders can significantly effect the response of the occluder to applied hemodynamic forces. If the pivots can be placed close to a diametral edge of the occluders, where the two occluders meet in close position, the effective lever arm of the occluder can be maximized. Moreover, the portion of the occluder from the pivot to the diametral edge can be minimized, thus reducing opposed torsional forces.

With the foregoing in mind, it is a principle object of my invention to provide a bi-leaflet heart valve with pivots as close to a diametral edge of the occluders of the valve as possible.

It has also been a object of my invention to provide a bi-leaflet heart valve which maximizes response to applied hemodynamic forces.

A further object of my invention has been to provide a bi-leaflet heart valve which opens and closes quickly to minimize hemodynamic losses across the valve.

These and other objects and features of my invention will be apparent from the following description taken with reference to the accompanying drawings.

SUMMARY OF MY INVENTION

I have invented a bi-leaflet heart valve having pivot ears comprising frustro-conical segments, located substantially at a diametral edge of leaflet occluders of the valve. Pivots on adjacent edges of both occluders share a common recess in an annular body of the valve. This configuration maximizes the response of the leaflets to applied hemodynamic forces. Consequently, the leaflets open and close quickly, minimizing hemodynamic loss across the valve.

DETAILED DESCRIPTION OF MY PREFERRED EMBODIMENT

I will now describe my invention by reference to the drawings. Like numerals designate like part throughout.

Figure 1:
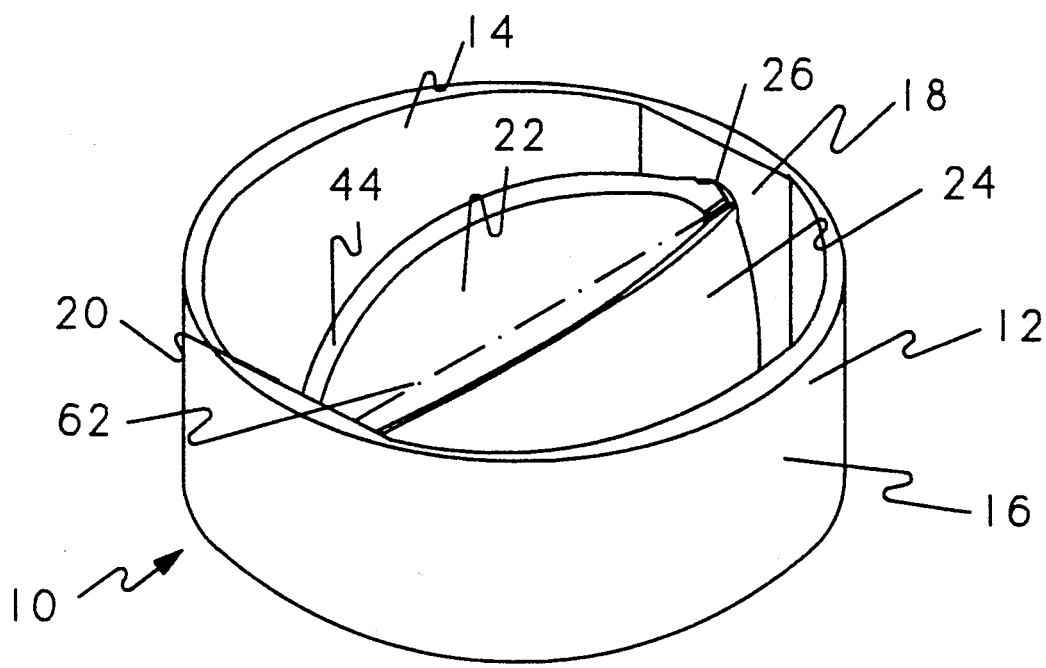
FIG. 1 is perspective view of a bi-leaflet heart valve prosthesis according to my present invention.
Figure 2:
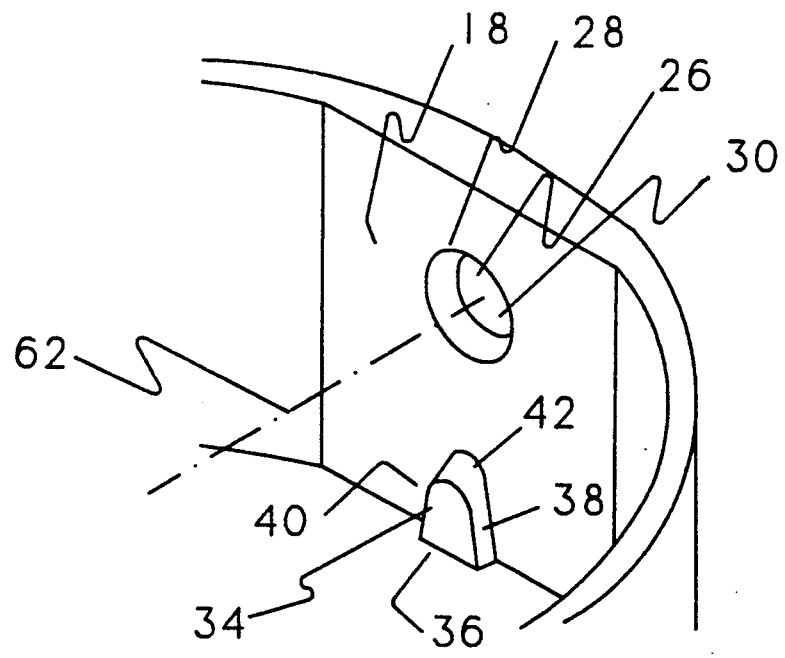
FIG. 2 is a partial perspective view of a portion of an annular body of the prosthesis of FIG. 1, showing a shared recess and stop.

FIG. 1 illustrates a bi-leaflet heart valve prosthesis, generally designated 10. The prosthesis 10 comprises an annular valve body 12 which has a generally cylindrical inner surface 14 and an outer surface 16. The outer surface 16 may be provided with conventional features, not shown herein, to adapt the prosthesis to receive various kinds of suture rings as is well known in this art. The inner surface 14 has two opposed cordial planes 18, 20. The cordial planes 18, 20 are parallel to each other and provide planar surfaces against which two leaflets occluders 22, 24 can pivot. In each of the cordial planes 18, 20 a single pivot recess is provided. A recess 26 can best be seen in FIG. 2. The recess is a surface of revolution about an axis which is a diameter of the valve body. I prefer a recess having the configuration of a truncated cone. An inclined circular surface 28 extends outwardly from the cordial surface 18 to a base 30. The base 30 is generally parallel to the cordial surface 18. Below the recess 26 at a lower edge of the annular valve body, I have placed a triangular stop 34. The stop 34 prevents the leaflets from opening to their fullest possible extent. Generally, forward flow through the valve, which opens the valve, is much more energetic than reverse flow. Forward flow is driven by the positive action of the heart, while reverse flow is a static pressure of the blood. It is advisable, therefore, to optimize the opening and closing conditions of the valve. By preventing the leaflet occluders from opening fully, a better closing action can be achieved. The stop comprises a wedge-shaped block having a base 36 and two opposed inclined sides 38, 40. The inclined sides 38, 40 connected a rounded vertex 42.

Figure 3:
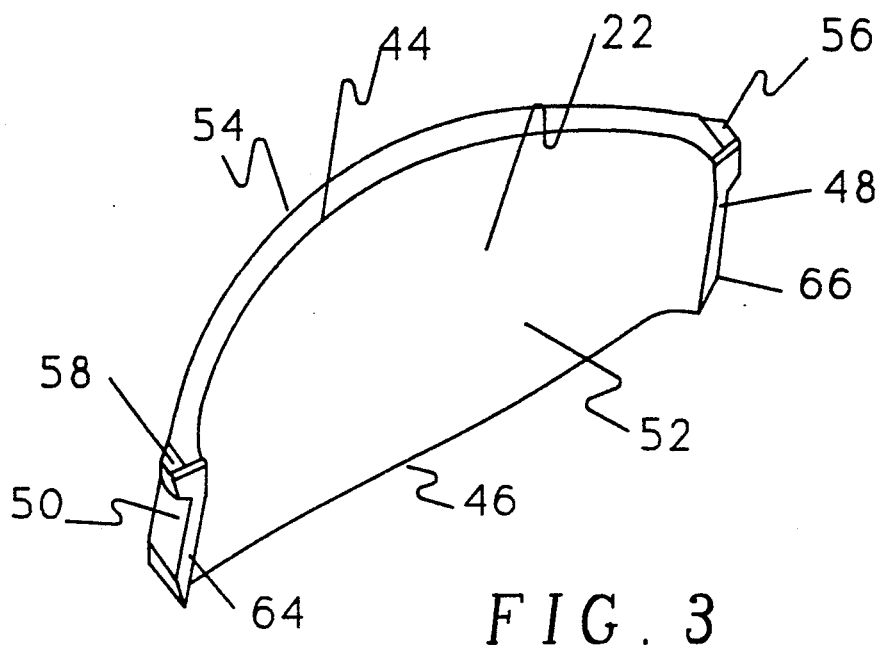
FIG. 3 is a perspective view of a leaflet occluder, with pivots according to my present invention.

I will now describe the leaflet occluders by reference to the leaflet occluder 22 shown in perspective view in FIG. 3. The leaflet occluder 22 comprises a diametral mating edge 44 and an arcuate edge 46. In the closed position, the diametral edges 44 of two occluders will mate along a diameter of the annular valve body while arcuate edge 46 of each occluder will close against the cylindrical inner surface 14 of the annular body. Between the diametral edge 44 and the arcuate edge 46, at each end of the occluder, there are straight cordial segments 48, 50. The cordial segments 48, 50 rest against the cordial planes 18, 20 of the annular body throughout the pivoting action of the occluders from their closed to open positions and back again. In my preferred embodiment, the leaflet occluders have a concave inner surface 52 and a convex outer surface 54. The degree of concavity and corresponding convexity of these two surfaces is relatively substantial, so that the gap between the two occluders when the occluders are in open position is significant, as shown in FIG. 1. A fairly large gap is desireable to minimize the possibility of cavitation which might theoretically occur if a narrow slit between the occluders was presented to blood flow.

Figure 4:
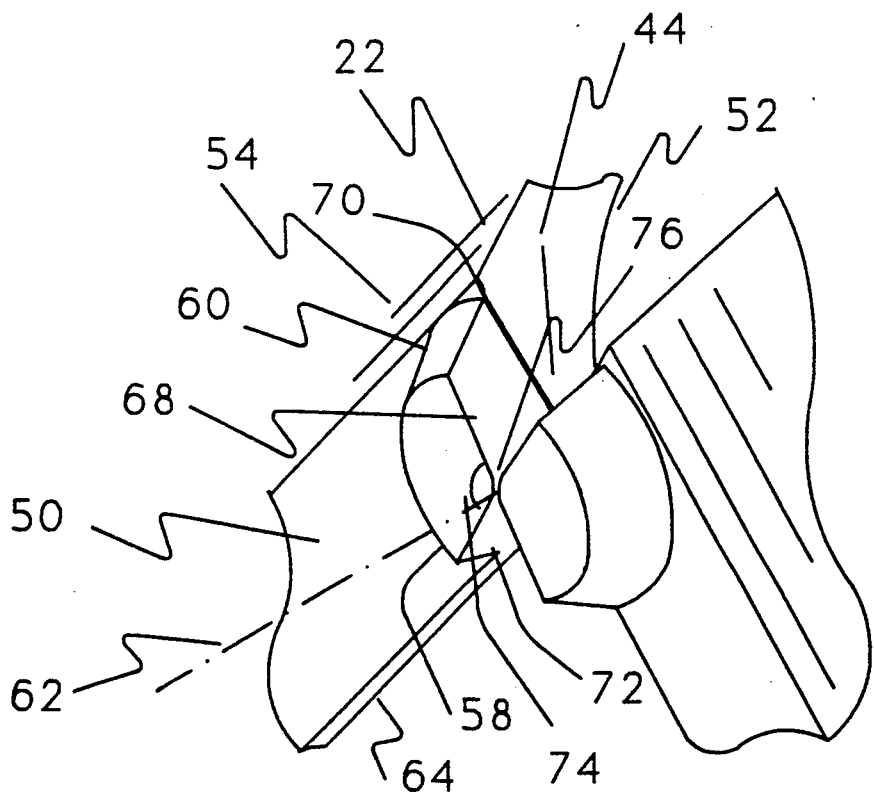
FIG. 4 is an enlarged perspective view of two pivots of two adjacent occluders.

At each of the cordial edges 48, 50 and immediately adjacent the diametral edge 44, I have provided a pivot ear 56, 58. The structure of these ears can best be seen in FIG. 4. In my preferred embodiment the ears, such as ear 58, comprise a frustro-conical segment, although other surfaces could be selected. A surface of revolution 60 is formed around an axis 62. The axis 62 is a diameter of the annular valve body 12 and is perpendicular to the straight edges 64, 66 of the leaflet 22 in assembled condition. The axis 62 will generally fall at the center of the recess, as shown if FIGS. 1 and 2. Clearly, other surfaces of revolution, besides conical, could be selected around the axis 62 without departing from the spirit or teachings of my invention.

The pivot ear 58 further comprises a mating face 68 which is substantially parallel to the plane of the diametral edge 44. The mating face 68 will be adjacent a similar mating edge on a corresponding pivot on the other leaflet 24 when the leaflet are in a closed position. To avoid impact of the pivot ears with each other as the leaflets close, it is possible to recess the mating faces 68 slightly so that a slight lip 70 is formed between the mating face 68 and the diametral edge 44. A non-mating face 72 is generally parallel to the edge 64. Since the opening motion of the leaflets will be halted by the stop 34, the nonmating faces 72 on the pivots will not collide. The mating face 68 and the nonmating face 72 of each leaflet would, if extended, intersect at the axis 62, forming an oblique angle 74. I have rounded the intersection of these faces, however, to form a rounded corner or vertex 76. The rounded corner 76 permits a certain play between the leaflets and permits the two pivots to roll against each other when pivoting between their open and closed positions. Moreover, it is known that a certain amount of space should be provided in pivots for mechanical heart valves so that blood can flush around the pivots. This flushing action minimizes the possibility of thrombus formation.

The pivot configuration of my invention, as described above, enables me to place the pivots of each leaflet occluder substantially at the diametral edge of each occluder. This means that the entire surface of the occluder will act as a positive lever arm and the occluders will move quickly between open and closed positions. None of the leaflet is inside the pivot point where it would act as a negative lever arm, resisting the desired motion of the valve. By placing the pivots in a shared recess, the response of the valve to opening and closing forces can be maximized.

The foregoing description describes my preferred embodiment of my invention, but my invention may be embodied in other specific forms without departing from the spirit and teachings thereof. My invention, therefore, is defined by the appended claims, and not by the foregoing description, and all embodiments within the meaning of equivalency of the claims are meant to be encompassed therein.

I claim as my invention:

1. A mechanical heart valve prosthesis comprising an annular valve body, said valve body defining a generally cylindrical central orifice;

two opposed recesses symmetrically placed on a diameter of said cylindrical orifice, each recess comprising a surface of revolution about said diameter;

two leaflet occluders, each occluder comprising a generally linear diametral edge and an arcuate edge, said diametral edges lying adjacent each other and said arcuate edges lying adjacent said annular valve body when said occluders are closed; and a pivot at each intersection of said diametral edge and said arcuate edge on each of said leaflet occluders, each of said pivots comprising (1) a curved outer surface, said curved outer surface consisting of partial surface of revolution which will slidingly engage said recess surface of revolution, (2) a first planar face substantially co-planar with said diametral edge, and (3) a second planar face, said first and second planar faces intersecting at a vertex forming an oblique interior angle, one pivot from one of said occluders sharing one of said recesses with one pivot from the other of said occluders, said second faces of said pivots in said shared recess lying adjacent each other when said occluders are open.

2. The mechanical heart valve according to claim 1 wherein the vertex of each pivot is rounded.

3. The mechanical heart valve according to claim 2 further comprising at least one stop on said annular valve body spaced away from said recesses, said stop having a first surface for contacting the arcuate edge of one of said occluders and a second surface for contacting the arcuate edge of the other of said occluders when said occluders reach on open position.

4. The mechanical heart valve according to claim 3 wherein each leaflet occluder further comprises a concave inner surface and a convex outer surface.

5. A mechanical heart valve prosthesis comprising
an annular valve body, said valve body defining a generally cylindrical central orifice;
two opposed recesses symmetrically placed on a diameter of said cylindrical orifice, each recess comprising a conical surface of revolution about said diameter;
two leaflet occluders, each occluder comprising a generally linear diametral edge and an arcuate edge, said diametral edges lying adjacent each other and said arcuate edges lying adjacent said annular valve body when said occluders are closed; and a pivot at each intersection of said diametral edge and said arcuate edge on each of said leaflet occluders, each of said pivots comprising a curved outer surface, said curved outer surface consisting of a segment of a cone which will slidingly engage said recess conical surface of revolution, a first face substantially co-planar with said diametral edge, and a second face, said first and second faces intersecting at a vertex forming an oblique interior angle, one pivot from one of said, occluders sharing one of said recesses with one pivot from the other of said occluders.

6. The mechanical heart valve according to claim 5 wherein the conical surface is a frustro-conical surface and wherein the segment of a cone is a frustro-conical segment.

7. The mechanical heart valve according to claim 6 wherein the first face of each pivot is off-set from said diametral edge.

8. The mechanical heart valve according to claim 7 wherein the vertex of each pivot is rounded.

9. The mechanical heart valve according to claim 8 further comprising at least one stop on said annular valve body spaced away from said recesses, said stop having a first surface for contacting the arcuate edge of one of said occluders and a second surface for contacting the arcuate edge of the other of said occluders when said occluders reach on open position.

10. The mechanical heart valve according to claim 9 wherein each leaflet occluder further comprises a concave inner surface and a convex outer surface.

* * * * *